United States Patent [19]

Taskis

[11] 4,223,006
[45] Sep. 16, 1980

[54] COATED PARTICLES

[75] Inventor: Charles B. Taskis, Worthing, England

[73] Assignee: Beecham Group Limited, England

[21] Appl. No.: 965,865

[22] Filed: Dec. 4, 1978

[30] Foreign Application Priority Data

Dec. 8, 1977 [GB] United Kingdom ............... 51058/77

[51] Int. Cl.² .......................... A61K 9/28; A61K 9/32
[52] U.S. Cl. ....................................... 424/16; 424/32; 424/33; 424/35
[58] Field of Search .................... 424/32–35, 424/16, 19, 22

[56] References Cited

U.S. PATENT DOCUMENTS

| | | | |
|---|---|---|---|
| 2,410,417 | 11/1946 | Andersen | 424/32 |
| 2,811,483 | 10/1957 | Aterno et al. | 424/32 |
| 3,089,824 | 5/1963 | Wurstor | 424/32 |
| 3,112,220 | 11/1963 | Heiser et al. | 424/35 |
| 3,400,185 | 9/1968 | Kohnle et al. | 424/35 |
| 3,553,313 | 1/1971 | Tort | 424/35 |
| 3,860,733 | 1/1975 | Morse et al. | 424/35 |
| 3,909,444 | 9/1975 | Anderson et al. | 424/35 |
| 3,968,277 | 7/1976 | Takase | 424/32 |
| 4,016,254 | 4/1977 | Seagor | 424/33 |
| 4,123,382 | 10/1978 | Morse et al. | 424/35 |

Primary Examiner—Shep K. Rose
Attorney, Agent, or Firm—Jacobs & Jacobs

[57] ABSTRACT

Pharmaceutically acceptable particles comprising an anhydrous hygroscopic salt of clavulanic acid dispersed in a polymeric binder of low water vapour permeability may be used in the preparation of pharmaceutical compositions of enhanced storage stability.

41 Claims, 1 Drawing Figure

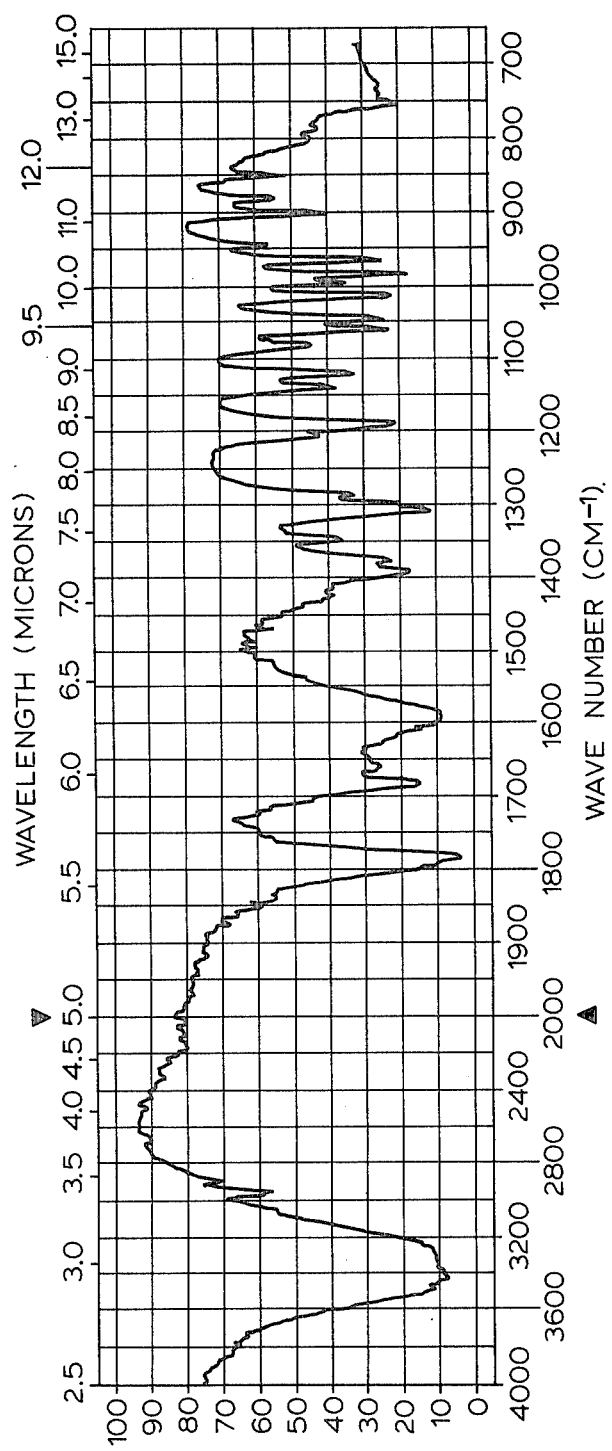

COATED PARTICLES

This invention relates to pharmaceutically acceptable particles containing salts of clavulanic acid.

U.K. Pat. No. 1508977 discloses inter alia the antibacterially active salts of clavulanic acid. Clavulanic acid has the formula (A):

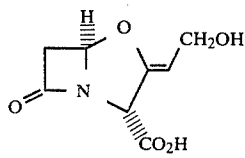
(A)

It has now been found that certain salts of clavulanic acid are sufficiently hygroscopic to pick up sufficient amounts of moisture during the period of their formulation into conventional pharmaceutical compositions to render those compositions somewhat less stable than might be desirable for long term storage.

It is an object of this invention to reduce this moisture pick up.

Accordingly, the present invention provides pharmaceutically acceptable particles comprising an anhydrous hygroscopic salt of clavulanic acid dispersed in a polymeric binder of low water vapour permeability.

It should be pointed out that U.K. Pat. No. 1508977 does disclose the use of an enteric coating agent with oral compositions of clavulanic acid and its salts. However the use suggested therein is as a coating layer around formulated compositions, such as tablets, to prevent these formulated compositions from having prolonged contact with highly acidic gastric juice. Nowhere in U.K. Pat. No. 1508977 is it in anyway disclosed or suggested that advantages can be obtained by dispersing certain of the clavulanic acid salts in polymeric binders of low water vapour permeability on a particulate scale.

The salts of clavulanic acid that are used in this invention must be anhydrous. Preferably the salts will contain less than 3% (w/w) moisture and more preferably less than 1% moisture as determined by methods estimating total water content such as Karl Fischer analysis or equivalent methods.

The salts of clavulanic acid used in this invention are those that are hygroscopic, a property understood and easily recognised by the skilled man. By way of illustration suitable salts are those which pick up atmospheric moisture at normal ambient Relative Humidities (R.H.) for example 10 to 50% R.H. The skilled man will know that over the usual range of ambient temperatures used in formulation hygroscopicity is temperature independent.

The salts of clavulanic acid that are suitable for use in this invention are those salts which contain non-toxic cations and which do not contain water of crystallisation. Suitable salts include the alkali and alkaline earth metal salts such as the sodium, potassium, calcium and magnesium salts. Most suitably the salts used in this invention will be crystalline alkali metal salts such as the crystalline sodium salt anhydrate (a typical infra-red spectrum of this material is shown herein in FIG. 1) and the crystalline potassium salt (which is an anhydrate).

The binder used in this invention is of low water vapour permeability, a property that is well known to those skilled in pharmaceutical formulation with binders. Suitable binders have a water vapour permeability at 40° C., 90% R.H., of less than $1 \times 10^{-8}$ g. cm/cm$^2$sec. cm.Hg., for example 2.5 to $3.0 \times 10^{-10}$ g. cm/cm$^2$sec cm.Hg. Often the binder will be water-insoluble. Suitable water-insoluble binders have a solubility of less than 0.5% (w/w) in water at any temperature between 15° to 30° C. in the pH range 5 to 8.

Suitable examples of such binders for use in this invention include semi-synthetic polymers, for example cellulose polymers such as ethyl cellulose and the like, and cellulose esters such as cellulose acetates and phthalates; synthetic polymers such as polymers and copolymers of acrylic acid, polymers and copolymers of methacrylic acid, and polyvinyl acetates; and natural gums and resins such as alginic acid and shellac; and the like. Mixtures of such binders may also be used.

Specific examples of cellulose esters are cellulose acetate phthalate (commercially available from Kodak, Eastman Chemical Products, Inc., Building 280, Kingsport, Tennessee 37662, U.S.A.) and hydroxypropylmethyl cellulose phthalate (commercially available from Shinetsu Chemical Company, 4-2,1-Chome Marunouchi, Chiyoda-ku, Tokyo, Japan.).

Specific examples of methacrylic acid copolymers are the Eudragit copolymers which are dimethylaminoethyl methacrylate copolymers, such as Eudragit RS-100 (commercially available from Rohm Pharma GMBH, 6100 Darmstadt, Postfach 4347, Bundesrepublik, Deutchland); and the M.P.A. - R.E. copolymer which is an amphoteric water-resistant 2-methyl-5-vinylpyridine methacrylic acid methylacrylate copolymer (commercially available from Tanabe Seiyako Co. Ltd., Osaka, Japan).

Specific examples of polyvinyl acetate polymers are polyvinyl acetate phthalate, which may be produced by the esterification of a partially hydrolysed polyvinyl acetate with phthalic anhydride (PVAP, commercially available from Colorcon Inc., Moyer Boulevard, West Point P.A. 19486, U.S.A.); and Sanyo A.E.A. which is polyvinyl acetaldehydiethylamino acetate (commercially available from Sankyo Co. Ltd., No. 7-12 Ginza 2-Chome, Chuo-ku, Tokyo, 104-Japan).

Particularly effective binders include ethyl cellulose and PVAP.

The particles of the invention are in the form of a matrix of the binder in which is dispersed the active ingredient. The exact physical structure of the particles will of course vary with the physical form of the clavulanic acid salt dispersed therein (for example crystals or an amorphous powder), the specific binder used, and the preparative process. Thus by way of example when the clavulanic acid salt used is the crystalline potassium salt then the particles made therefrom can be loose or compact agglomerates of needlelike coated crystals depending on the binder and the preparative process used.

The particles of the invention will normally have a size in the range 10 to 500$\mu$, more generally 15 to 200$\mu$, for example 20 to 100$\mu$; and will normally comprise 5 to 75% binder, for example 15 to 50% binder.

The surface of the particles of the invention should not normally present more than about 10% (area/area) of salt of clavulanic acid. The remaining surface area will normally be binder.

From the aforesaid it will be realised that preferred particles of this invention include particles of size 10 to 500$\mu$ comprising anhydrous crystalline potassium clavulanate dispersed in PVAP; the PVAP representing 15 to 50% of the particles.

The particles of the invention are normally kept as water-free as possible, and this may be effected in conventional manner by storing in the presence of a dehydrating agent.

The particles of this invention may be formulated into pharmaceutical compositions in conventional manner with less moisture pick up than with the corresponding untreated clavulanic acid salt.

The particles of the invention may be prepared by a process which comprises depositing the binder on the salt of clavulanic acid, under substantially anhydrous conditions.

This process may be carried out in a number of conventional ways.

For example an anhydrous suspension of the active ingredient in a solution of the binder may be spray-dried by conventional techniques, e.g. as described in U.K. Pat. No. 1403584. Examples of suitable solvents for such a process include volatile organic solvents such as dichloromethane or trichloroethylene.

Co-acervation may also be used, for example as described in U.S. Pat. Nos. 3,336,155 and 3,531,418. By way of example, the particles of the invention may be prepared by coacervation by suspending the active ingredient in a non-solvent therefor (but a solvent for the binder), dissolving the binder in this suspension, and then inducing precipitation of the desired particles by temperature reduction or by addition of a non-solvent for the binder (and suspended active ingredient).

In general it is preferred that the process used results in particles of the desired size, as the use of conventional size reduction techniques such as milling may result in substantial exposed surfaces of salt of clavulanic acid being formed. With this proviso, conventional granulation techniques such as wet granulation can be used, but are less suitable. However there are certain specific granulation techniques that can be used with advantage, and these include fluid bed granulation (in which fluidised active ingredient is sprayed with a solution of the binder in a volatile anhydrous solvent), as in these techniques the size of the product can be more readily controlled.

The particles of the invention are used for formulation into conventional solid dosage forms such as tablets, capsules, powders and the like, and will normally be adapted for oral administration.

Thus the invention also provides a pharmaceutical composition, which composition comprises the particles of the invention.

The compositions of this invention may be prepared from the particles of this invention in entirely conventional manner.

Tablets and capsules for oral administration may be in unit dose presentation form, and may contain pharmaceutically acceptable excipients such as binding agents, fillers, tabletting lubricants, disintegrants, and acceptable wetting agents and the like in addition to the particles of the invention. The tablets may be coated according to methods well known in normal pharmaceutical practice. Powders for reconstitution with water or other suitable vehicle before use may contain pharmaceutically acceptable additives such as suspending agents, emulsifying agents, preservatives, and if desired conventional flavouring or colouring agents, and the like.

The compositions of the invention are suitably prepared from the particles of the invention under conditions of low humidity, and the compositions once prepared are suitably stored under conditions of low humidity.

The pharmaceutical compositions of the invention may suitably contain a penicillin or cephalosporin.

Suitable penicillins and cephalosporins for use in such compositions include those described in U.K. Pat. No. 1508977. Particularly suitably penicillins and cephalosporins for use include talampicillin hydrochloride, pivampicillin hydrochloride, bacampicillin hydrochloride, amoxycillin trihydrate, sodium and potassium amoxycillin, carbenicillin α-phenyl ester sodium salt, carbenicillin α-indanyl ester sodium salt, ticarcillin α-phenyl ester sodium salt, cephalexin, cephaloglycine, cephradin, and the like. They also include anhydrous ampicillin, ampicillin trihydrate and sodium ampicillin.

Particularly favoured penicillins for inclusion in such compositions include amoxycillin trihydrate, sodium and potassium amoxycillin. They also include ampicillin trihydrate, sodium ampicillin and ampicillin anhydrate.

Preferred penicillins for inclusion in such compositions include amoxycillin trihydrate, sodium and potassium amoxycillin.

A particularly preferred penicillin for inclusion in such compositions is amoxycillin trihydrate. It is especially surprising that compositions containing amoxycillin trihydrate are so stable in view of the hydrated nature of this penicillin.

In such compositions the weight ratio (as free acids) of the penicillin or cephalosporin to the clavulanic acid salt is suitably 5:1 to 1:1, for example about 2:1 or 3:1.

The pharmaceutical compositions of this invention are more stable on long term storage than are corresponding compositions containing free clavulanic acid salts.

The invention also provides a method of treatment of bacterial infection which comprises the administration to the sufferer of a pharmaceutical composition according to this invention.

Suitable dosage regimes are fully described in U.K. Pat. No. 1508977.

The following Examples illustrate the various aspects of this invention:

EXAMPLE 1

Preparation of crystalline sodium clavulanate anhydrate, for use according to the invention Anhydrous (freeze-dried) sodium clavulanate (10 g) was dissolved in NN-dimethylacetamide (200 ml) at room temperature. The solution was filtered and the filtrate precipitated with methylene dichloride (2500 ml) at room temperature. The solution was filtered through glass wool (or other coarse filter) to remove the initial precipitate and the filtrate allowed to stand for 24 hours at 0° C. to 5° C., after which time a flaky white precipitate was observed and harvested. The product was washed with methylene dichloride (1000 ml) to yield a light white powder.

The i.r. spectra of this product is shown on FIG. 1.

EXAMPLE 2

Sodium clavulanate dispersed in ethyl cellulose, by coacervation 50 mls of a 4% (w/v) solution of ethyl cellulose in dichloromethane were mixed with 50 mls of petroleum spirit (40–60), and further petroleum spirit added until a slight turbidity appeared. 6 g. of anhydrous crystalline sodium clavulanate anhydrate (prepared as in Example 1) was added and a further 250 mls of petroleum spirit added with energetic stirring. The solid was filtered off, washed and dried.

The resultant particles have a reduced affinity for moisture. When exposed to air of 44% relative humidity at 20° C. for 24 hours they gained 3.5% w/w moisture, corresponding to a 4.7% w/w weight gain by the crystalline sodium clavulanate anhydrate. This compares with a 32% w/w weight gain by uncoated crystalline sodium clavulanate anhydrate under the same conditions when hydrating to the tetrahydrate.

The resultant particles have a rapid dissolution rate in water.

EXAMPLE 3

Sodium clavulanate dispersed in ethyl cellulose, by spray drying 50 g anhydrous crystalline sodium clavulanate anhydrate (prepared as described in Example 1) was suspended in 250 ml of a trichloroethylene solution containing 25 g ethyl cellulose (N4 grade). The suspension was well mixed and spray dried, using inlet and outlet temperatures of 150° C. and 90° C. respectively. The product was composed of small particles having a smooth outer surface with reduced water permeability.

EXAMPLE 4

Potassium clavulanate dispersed in polyvinyl acetate phthalate (PVAP), by coacervation 25 mls of a 10% w/v solution of PVAP in methanol were mixed with 300 mls dichloromethane and further dichloromethane added until a slight turbidity appeared. 10 g. crystalline potassium clavulanate were added and a further 300 mls dichloromethane added with vigourous mixing (Silverson mixer). The solid was filtered off, washed in dichloromethane and dried at room temperature under vacuum.

EXAMPLE 5

Potassium clavulanate dispersed in Eudragit RS-100 (a dimethylaminoethylmethacrylate polymer), by coacervation 50 mls of a 5% w/v solution of Eudragit RS-100 in dichloromethane were mixed with 50 mls heptane with which a slight turbidity appeared. 10 g. crystalline potassium clavulanate were added and a further 500 mls heptane with vigourous mixing (Silverson mixer). The solid was filtered off, washed in heptane and dried at room temperature under vacuum.

EXAMPLE 6

Potassium clavulanate dispersed in 2-methyl-5-vinylpyridine methacrylic acid methacrylate copolymer (MPA-RE), by coacervation 100 mls of a 2.5% w/v MPA-RE in 1:1 propan-2-ol dichloromethane solution were mixed with 20 mls acetone and further acetone added until a slight turbidity appeared. 10 g. crystalline potassium clavulanate were added and a further 250 mls acetone added with vigourous mixing (Silverson mixer). The solid was filtered off, washed in acetone and dried at room temperature under vacuum.

EXAMPLE 7

Potassium clavulanate dispersed in hydroxypropyl methylcellulose phthalate (HPMCP), by coacervation 100 mls of a 2.5% w/v HPMCP in dichloromethane solution were mixed with 50 mls acetone producing a slight turbidity. 10 g crystalline potassium clavulanate were added and a further 700 mls acetone added with vigourous mixing (Silverson mixer). The solid was filtered off, washed in acetone and dried at room temperature under vacuum.

EXAMPLE 8

Approximately 1 gm. portions of materials prepared as in each of Examples 4 to 7 were exposed to 44% and 55% R.H. (Relative Humidity) at 20° C. for periods up to 30 hours (24 hours is a typical period taken for conventional formulation).

In all cases these materials showed substantially less % weight gain due to moisture pick-up than did corresponding portions of crystalline potassium clavulanate under identical conditions.

EXAMPLE 9

Each of the materials prepared according to Examples 2 to 7 dispersed rapidly in simulated gastric juices at 37° C. to yield a solution of the active ingredient.

EXAMPLE 10

Each of the materials prepared according to Examples 2 to 7 were separately mixed with sufficient amoxycillin trihydrate to give a 2:1 weight ratio (as free acids) of penicillin to clavulanic acid salt.

EXAMPLE 11

Each of the formulations prepared as in Example 10 were separately mixed with a lubricant (magnesium stearate) and a disintegrant (microcrystalline cellulose) and filled into No. O hard gelatine capsules.

The relative preportions of the ingredients and the weight filled into each capsule was such that each capsule contained:
 300 mg. of amoxycillin trihydrate
 200 mg. of coated clavulanic acid salt particles
 5 mg. of magnesium stearate
 15 mg. of micro crystalline cellulose

What we claim is:

1. Pharmaceutically acceptable particles comprising an anhydrous hygroscopic salt of clavulanic acid dispersed in a polymeric binder having a water vapour permeability at 40° C., 90% R. H. of less than $1 \times 10^{-8}$ g cm/cm$^2$ sec. cm. Hg.

2. Particles according to claim 1, wherein the salt of clavulanic acid is the crystalline sodium salt anhydrate having the infra-red spectrum as shown herein in FIG. 1, or the crystalline potassium salt.

3. Particles according to claim 1 or 2, wherein the binder is a cellulose polymer, a polymer or copolymer of acrylic acid, a polymer or copolymer of methacrylic acid, or a polyvinyl acetate polymer.

4. Particles according to claim 3, wherein the binder is ethyl cellulose or polyvinyl acetate phthalate.

5. Particles according to claim 1, wherein the binder is water-insoluble.

6. Particles according to claim 1, of size 10 to 500μ.

7. Particles according to claim 1, of size 10 to 500μ comprising anhydrous crystalline potassium clavulanate dispersed in polyvinyl acetate phthalate; the polyvinyl acetate phthalate representing 15 to 50% of the particles.

8. A process for the preparation of the particles according to claim 1, which process comprises depositing the binder on the salt of clavulanic acid, under substantially anhydrous conditions.

9. Particles according to claim 1 wherein the salt of clavulanic acid contains non-toxic cations and does not contain water of crystallization.

10. Particles according to claim 9 wherein the salt of clavulanic acid is an alkaline metal salt.

11. Particles according to claim 10 wherein the alkaline metal salt is crystalline.

12. Particles according to claim 9 wherein the salt of clavulanic acid is an alkaline earth metal salt.

13. Particles according to claim 9 wherein the salt of clavulanic acid is the sodium, potassium, calcium or magnesium salt.

14. A pharmacetical composition useful for treating bacterial infections in humans and animals which comprises pharmaceutically acceptable particles comprising an anhydrous hydroscopic salt of clavulanic acid dispersed in a polymeric binder having a water vapour permeability at 40° C., 90% R.H. of less than $3 \times 10^{-8}$ g cm/cm$^2$ sec. cm. Hg, in combination with a pharmaceutically acceptable carrier.

15. A composition according to claim 14 wherein the salt of clavulanic acid is the crystalline sodium salt anhydrate having the infra-red spectrum as shown herein FIG. 1, or the crystalline potassium salt.

16. A composition according to claim 15 wherein the binder is a cellulose polymer, a polymer or copolymer of acrylic acid, a polymer or copolymer of methacrylic acid, or a polyvinyl acetate polymer.

17. A composition according to claim 16 wherein the binder is ethyl cellulose or polyvinyl acetate phthalate.

18. A composition according to claim 14 wherein the binder is water-insoluable.

19. A composition according to claim 14 wherein the particles have a size of 10 to 500μ.

20. A composition according to claim 14 wherein the particles have a size of 10 to 500μ and comprise anhydrous crystalline potassium clavulanate dispersed in polyvinyl acetate phthalate, the polyvinyl acetate phthalate representing 15 to 50% of the particles.

21. A composition according to claim 14 wherein the salt of clavulanic acid contains non-toxic cations and does not water of crystallization.

22. A composition according to claim 14 wherein the salt of clavulanic acid is an alkaline metal salt.

23. A composition according to claim 22 wherein the alkaline metal is crystalline.

24. A composition according to claim 14 wherein the salt of clavulanic acid is an alkaline earth metal salt.

25. A composition according to claim 14 wherein the salt of clavulanic acid is the sodium, potassium, calcium or magnesium salt.

26. A method of treating bacterial infections in humans and animals which comprises administering to a human or animal in need thereof, an antibacterially effective amount of pharmaceutically acceptable particles comprising an anhydrous hydroscopic salt of clavulanic acid dispersed in a polymeric binder having a water vapour permeability at 40° C., 90% R.H. of less than $1 \times 10^{-8}$ g cm/cm$^2$ sec. cm. Hg.

27. A method according to claim 26 wherein the salt of clavulanic acid is the crystalline sodium salt anhydrate having the infra-red spectrum as shown herein FIG. 1, or the crystalline potassium salt.

28. A method according to claim 27 wherein the binder is a cellulose polymer, a polymer or copolymer of acrylic acid, a polymer or copolymer of methacrylic acid, or a polyvinyl acetate polymer.

29. A method according to claim 28 wherein the binder is ethyl cellulose or polyvinyl acetate phthalate.

30. A method according to claim 26 wherein the binder is water-insoluable.

31. A method according to claim 26 wherein the particles have a size of 10 to 500μ.

32. A method according to claim 26 wherein the particles have a size of 10 to 500μ and comprise anhydrous crystalline potassium clavulanate dispersed in polyvinyl acetate phthalate; the polyvinyl acetate phthalate representing 15 to 50% of the particles.

33. A method according to claim 26 wherein the salt of clavulanic acid contains non-toxic cations and does not water of crystallization.

34. A method according to claim 26 wherein the salt of clavulanic acid is an alkaline metal salt.

35. A composition according to claim 34, wherein the weight ratio (as free acids) of the penicillin or cephalosporin to the clavulanic acid salt is 5:1 to 1:1.

36. A composition according to claim 34, wherein the penicillin or cephalosporin is amoxycillin trihydrate.

37. A method according to claim 34 wherein the alkaline metal salt is crystalline.

38. A method according to claim 26 wherein the salt of clavulanic acid is an alkaline earth metal salt.

39. A method according to claim 26 wherein the salt of clavulanic acid is the sodium, potassium, calcium or magnesium salt.

40. A pharmaceutical composition useful for treating bacterial infections in humans and animals which comprises a synergistically effective amount of pharmaceutically acceptable particles comprising anhydrous hydroscopic salt of clavulanic acid dispersed in a polymeric binder having a water vapour permeability at 40° C., 90% R.H. of less than $1 \times 10^{-8}$ g cm/cm$^2$ sec. cm. Hg and an antibacterially effective amount of a penicillin or a cephalosporin, in combination with a pharmaceutically acceptable carrier.

41. A method of treating bacterial infections in humans and animals which comprises administering to a human or animal in need thereof, a synergistically effective amount of pharmaceutically acceptable particles comprising anhydrous hydroscopic salt of clavulanic acid dispersed in a polymeric binder having a water vapour permeability at 40° C., 90% R.H. of less than $1 \times 10^{-8}$ g cm/cm$^2$ sec. cm. Hg and an antibacterially effective amount of a penicillin or cephalosporin.

* * * * *